(12) United States Patent
Dueva-Koganov et al.

(10) Patent No.: US 8,263,045 B2
(45) Date of Patent: *Sep. 11, 2012

(54) SUNLESS TANNING COMPOSITION AND METHOD OF SUNLESS TANNING

(75) Inventors: Olga Dueva-Koganov, White Plains, NY (US); Thomas Russo, Butler, NJ (US); James P. Sanogueira, Suffern, NY (US)

(73) Assignee: Playtex Products, Inc., Westport, CT (US)

( * ) Notice: Subject to any disclaimer, the term of this patent is extended or adjusted under 35 U.S.C. 154(b) by 259 days.

This patent is subject to a terminal disclaimer.

(21) Appl. No.: 12/154,524

(22) Filed: May 23, 2008

(65) Prior Publication Data

US 2008/0317680 A1  Dec. 25, 2008

(51) Int. Cl.
*A61K 8/00* (2006.01)
*A61K 8/18* (2006.01)
*A61K 9/00* (2006.01)
*A61Q 17/04* (2006.01)

(52) U.S. Cl. .......................................... 424/47; 424/59
(58) Field of Classification Search .................. None
See application file for complete search history.

(56) References Cited

U.S. PATENT DOCUMENTS

| | | | |
|---|---|---|---|
| 2,949,403 A | 8/1960 | Andreadis et al. | |
| 4,293,542 A | 10/1981 | Lang et al. | |
| 4,786,367 A | 11/1988 | Bogart et al. | |
| 5,211,883 A | 5/1993 | Yamashina et al. | |
| 5,268,166 A | 12/1993 | Barnett et al. | |
| 5,318,774 A * | 6/1994 | Alban et al. | 424/59 |
| 5,569,460 A | 10/1996 | Kurz et al. | |
| 5,626,839 A | 5/1997 | Scales-Medeiros | |
| 5,645,822 A | 7/1997 | Meyer et al. | |
| 5,747,435 A * | 5/1998 | Patel | 510/119 |
| 5,750,092 A | 5/1998 | Meyer et al. | |
| 5,750,094 A | 5/1998 | Tomomasa et al. | |
| 5,756,075 A | 5/1998 | Meyer | |
| 5,914,116 A | 6/1999 | Suares et al. | |
| 5,942,212 A | 8/1999 | Lentini et al. | |
| 6,113,888 A | 9/2000 | Castro et al. | |
| 6,117,433 A | 9/2000 | Edens et al. | |
| 6,126,924 A | 10/2000 | Scales-Medeiros et al. | |
| 6,199,557 B1 | 3/2001 | Laughlin | |

(Continued)

FOREIGN PATENT DOCUMENTS

EP  0 547 864  6/1993

(Continued)

OTHER PUBLICATIONS

Internet Website Address: http://feelconfident.co.uk/body-drench-whipped-chocolate-Selftanning-Mousse-5-fl-oz.com for Body Drench Whipped Chocolate Self-Tanning Mousse 5 Fl. Oz. (147MI), 2003-2006 Babylon Technologies Ltd.

(Continued)

*Primary Examiner* — Fereydoun G Sajjadi
*Assistant Examiner* — David Browe
(74) *Attorney, Agent, or Firm* — Ohlandt, Greeley, Ruggiero & Perle, L.L.P.

(57) ABSTRACT

A sunless tanning composition having dihydroacetone and an amphoglycinate (amphoacetate) in an amount effective for sunless tanning is provided. Also provided is a method of sunless tanning having the step of topically applying to the skin an effective amount of a sunless tanning composition having dihydroacetone and an amphoglycinate.

17 Claims, 2 Drawing Sheets

U.S. PATENT DOCUMENTS

| | | | |
|---|---|---|---|
| 6,305,384 B2 | 10/2001 | Laughlin | |
| 6,348,202 B1 | 2/2002 | Wadle | |
| 6,372,234 B1 | 4/2002 | Deckers et al. | |
| 6,416,747 B1 | 7/2002 | Laughlin | |
| 6,428,799 B1 | 8/2002 | Cen et al. | |
| 6,431,180 B2 | 8/2002 | Laughlin | |
| 6,432,895 B1 | 8/2002 | Bigorra et al. | |
| 6,439,243 B2 | 8/2002 | Laughlin | |
| 6,446,635 B2 | 9/2002 | Laughlin | |
| 6,468,508 B1 | 10/2002 | Laughlin | |
| 6,474,343 B2 | 11/2002 | Laughlin | |
| 6,552,207 B2 * | 4/2003 | Razzano | 554/68 |
| 6,723,306 B2 | 4/2004 | Gueret | |
| 7,378,084 B2 * | 5/2008 | Dueva-Koganov et al. | 424/59 |
| 2001/0003283 A1 | 6/2001 | Laughlin | |
| 2001/0018527 A1 | 8/2001 | Razzano | |
| 2002/0015683 A1 | 2/2002 | Nichols et al. | |
| 2002/0034489 A1 | 3/2002 | Wiegland et al. | |
| 2002/0037303 A1 | 3/2002 | Deckers et al. | |
| 2002/0071852 A1 | 6/2002 | Deckers et al. | |
| 2002/0106337 A1 | 8/2002 | Deckers et al. | |
| 2002/0114820 A1 | 8/2002 | Deckers et al. | |
| 2003/0224955 A1 | 12/2003 | Ribery et al. | |
| 2004/0013617 A1 * | 1/2004 | Rick et al. | 424/59 |
| 2004/0126342 A1 | 7/2004 | Dicianna | |
| 2005/0002978 A1 | 1/2005 | Crook et al. | |
| 2005/0089486 A1 | 4/2005 | Spindler et al. | |

FOREIGN PATENT DOCUMENTS

| | | |
|---|---|---|
| EP | 1541124 A1 | 6/2005 |
| EP | 1690521 A1 | 8/2006 |
| JP | 7-101843 A | 4/1995 |
| JP | H08-503961 A | 4/1996 |
| JP | 2005-519126 A | 6/2005 |
| JP | 2007-523869 A | 8/2007 |
| WO | 2007/005741 A2 | 1/2007 |

OTHER PUBLICATIONS

International Search Report based on PCT/US2006/25829, dated Aug. 22, 2007.
Japanese Notice of Reasons for Rejection dated Nov. 24, 2010 for corresponding Japanese Patent Application No. 2008-519660 with English translation.
Australian Examiner's Report dated Oct. 26, 2010 for corresponding Australian Patent Application No. 2006265816.
Mexican Official Action dated Jan. 20, 2011 for corresponding Mexican Patent Application No. MX/a/2008/000270 with English translation.
Mexican Official Action dated Sep. 1, 2010 for corresponding Mexican Patent Application No. MX/a/2008/000270 with English translation.
European Examination Report dated Apr. 21, 2011 for corresponding European Patent Application No. 06799990.4.
European Search Report dated Oct. 17, 2008 for corresponding European Patent Application No. 06799990.4.
Chinese Office Action dated May 25, 2011 for corresponding Chinese Patent Application No. 200680030318.8 with English translation.
Chinese Office Action dated Jun. 25, 2010 for corresponding Chinese Patent Application No. 200680030318.8 with English translation.
Australian Examiner's Report dated Jun. 15, 2010 for corresponding Australian Patent Application No. 2006265817.
Canadian Office Action dated Oct. 25, 2010 for corresponding Canadian Patent Application No. 2,613,510.
Canadian Office Action dated Nov. 4, 2009 for corresponding Canadian Patent Application No. 2,613,510.
Canadian Office Action dated Jul. 2, 2008 for corresponding Canadian Patent Application No. 2,613,510.
English translation of Mexican Official Action dated Aug. 7, 2009 for corresponding Mexican Patent Application No. MX/a/2008/000234.
Canadian Office Action dated Jul. 7, 2011 for corresponding Canadian Patent Application No. 2,613,504.
Canadian Office Action dated Oct. 25, 2010 for corresponding Canadian Patent Application No. 2,613,504.
Canadian Office Action dated Nov. 18, 2009 for corresponding Canadian Patent Application No. 2,613,504.
Chinese Office Action dated Nov. 6, 2009 for corresponding Chinese Patent Application No. 200680030260.7 with English translation.
Written Opinion dated Aug. 22, 2007 for corresponding International Patent Application No. PCT/US2006/025829.
International Preliminary Report on Patentability dated Nov. 7, 2007 for corresponding International Patent Application No. PCT/US2006/025830.
Search Report dated Sep. 25, 2007 for corresponding International Patent Application No. PCT/US2006/025830.
Notification of Second Office Action dated Mar. 26, 2012 from Application No. 200680030260.7.
Supplementary European Search Report dated May 31, 2012 from Application No. EP 06 77 4419.

* cited by examiner

SUNLESS TANNING COMPOSITION AND METHOD OF SUNLESS TANNING

BACKGROUND OF THE INVENTION

1. Field of the Invention

The present invention relates to a sunless tanning composition and its use in sunless tanning products. More particularly, the present invention relates to a method of sunless tanning that employs the sunless tanning composition according to the present invention and provides fast development of uniform, more intense, long-lasting and natural looking tan with more predictable, i.e., customized, color characteristics.

2. Description of the Related Art

U.S. Pat. Nos. 5,645,822 and 5,750,092 to Schering-Plough and European Patent Application No. 0 547 864 A1 describe attempts to provide sunless tanning. However, these and other approaches described in the art have certain drawbacks.

Products that are currently used for sunless tanning of the skin are based on the reaction of an active chemical present in the product with the skin amino acids. Such chemicals are well known and include compounds having an aldehyde group, or compounds having a ketone group, such as, for example, Dihydroacetone.

As an example, DHA gives skin a brownish color by reacting with the amino acids present in the sebum and stratum corneum by a known mechanism, namely the Maillard reaction.

Further, distribution and nature of the amino acids is not uniform on the surface of the skin and because of that the intensity and shade of the color obtained may vary from one place to another on the treated skin thereby causing the skin to have an unnatural look.

Further still, the duration of time required for development of skin color may be too long, which can lead to a decrease in the concentration of DHA on the surface of skin due to sweating or as a result of contact with clothing thereby staining the clothing and resulting in an uneven color development on the skin.

Thus, it is very desirable to obtain a uniform and natural looking sunless tan over all skin surfaces that are treated with a sunless tanning composition that can develop faster and last longer than formulations known in the art.

Thus, there is a need in consumer products and cosmetic industry for formulations that can enhance the effectiveness of the active ingredient used in sunless tanning and deliver increased performance characteristics and eliminate the need for exposure to damaging rays of the sun for tanning.

SUMMARY OF THE INVENTION

It is an object of the present invention to provide a sunless tanning composition having dihydroacetone and an amphoglycinate, also known as "amphoacetate," in amounts effective for sunless tanning.

It is another objective of the present invention to provide a sunless tanning composition that can develop faster than the known formulations.

It is still another object of the present invention to provide a method of sunless tanning having the step of topically applying to the skin an effective amount of a sunless tanning composition having dihydroacetone and an amphoglycinate.

It is yet another object of this invention to provide a sunless tanning product, such as, solution, emulsion, serum, lotion, skin cleanser, body wash, body scrub, bar soap, liquid soap, skin care preparation, foam, mousse, cream, lotion, pomade, balm, stick, gel, pump spray, and aerosol spray, and combinations thereof.

Accordingly, the present invention provides a sunless tanning composition having dihydroacetone and an amphoglycinate in amounts effective for sunless tanning.

The present invention further provides a method of sunless tanning having the step of topically applying to the skin an effective amount of a sunless tanning composition having dihydroacetone and an amphoglycinate.

Sunless tanning compositions containing dihydroxyacetone (DHA) are improved by the addition of amphoglycinates, either simultaneously, for example by mixing therewith, or sequentially by applying the amphoglycinates, for example, alternatingly therewith.

These and other objects and advantages of the present invention are achieved by the use of the sunless tanning compositions and method of sunless tanning according to the present invention to provide effective sunless tanning.

DETAILED DESCRIPTION OF THE INVENTION

Figure 1:
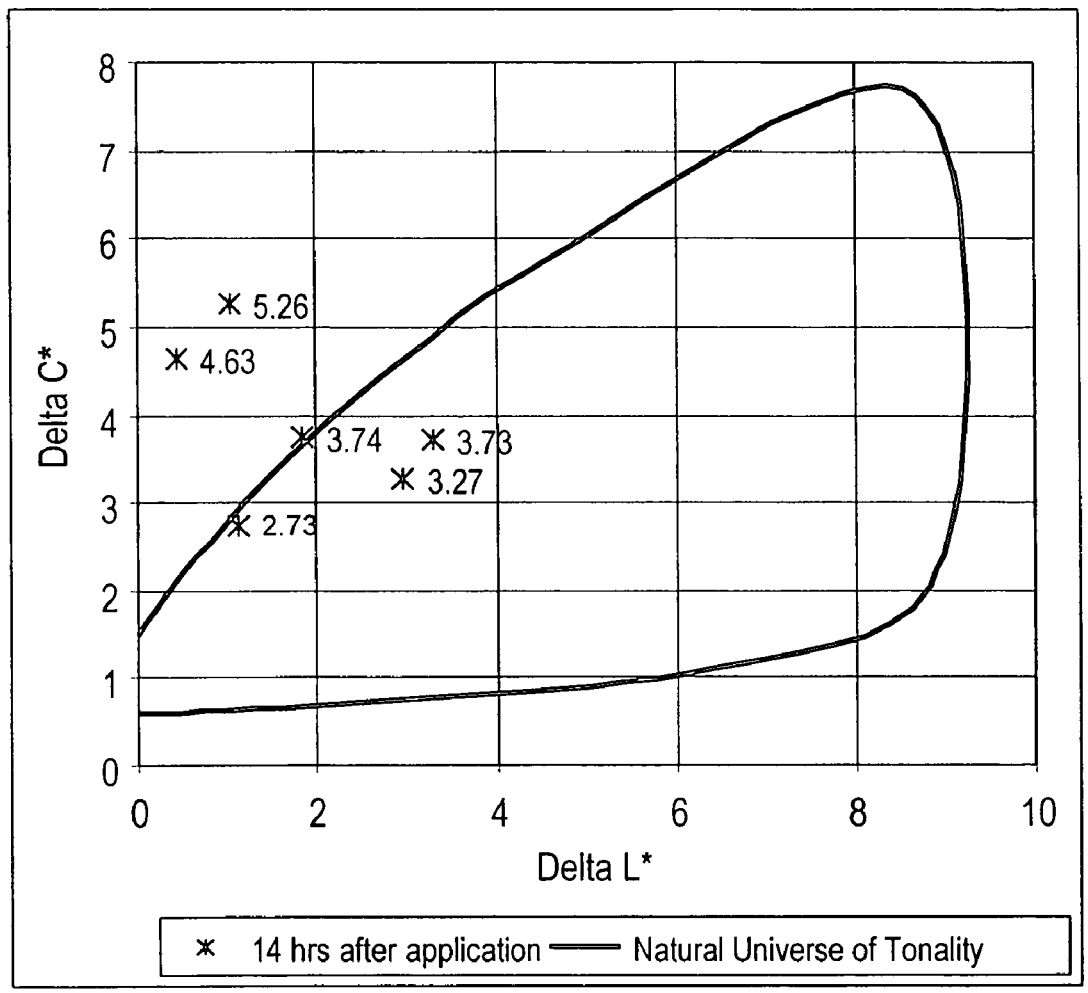
FIG. 1 is CIELAB plot of Delta C* versus Delta L*. It shows total chroma and lightness gradients of the skin treated with DHA-product alone or in conjunction with amphoacetates.

The present invention provides a sunless tanning composition having dihydroacetone and an amphoglycinate in amounts effective for sunless tanning.

Dihydroacetone is a known tanning agent, which exists in dimeric form. Typically, it is stored and often used as the phosphate salt. The monomer form has the chemical name of 1,3-dihydroxyacetone or 1,3-dihydroxy-2-propanone and is represented by the formula:

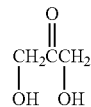

Sunless tanning compositions according to the present invention are improved by adding amphoglycinates (amphoacetates) sequentially or simultaneously to compositions containing dihydroxyacetone (DHA).

As mentioned herein above, amphoglycinates are also known as amphoacetates.

The terms "amphoglycinate" and "amphoacetate" have been used interchangeably in the art, as they are in the present application.

Amphoglycinates can be represented by the formula:

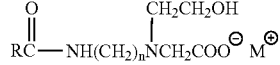

wherein the RC=O group represents the fatty acid residue derived from the specific oils or mixtures of oils used.

Thus, R can be a linear or branched $C_{10}$ to $C_{24}$ alkyl, any ranges therebetween or any mixtures thereof; wherein M is an alkali metal, such as, Li, Na, K and Cs; and n is an integer from 2 to 6.

In a preferred embodiment, n is 2 and the amphoglycinate is represented by the formula:

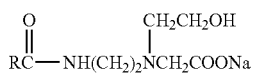

wherein R is a $C_{12}$ to $C_{22}$ alkyl. More preferably, R is a $C_{14}$ to $C_{20}$ alkyl and most preferably, R is a mixture of alkyls selected from linear and branched $C_{10}$ to $C_{24}$ alkyls and any ranges therebetween.

The amphoglycinate can be sodium oliveamphoacetate, sodium sunflowerseed amphoacetate, sodium cocoabutter amphoacetate, sodium sesame amphoacetate, sodium sweetalmond amphoacetate, sodium caproamphoacetate, sodium capryloamphoacetate, sodium isostearoamphoacetate, sodium lauroamphoacetate, sodium myristoamphoacetate, sodium oleoamphoacetate, sodium palmamphoacetate, sodium peanutamphoacetate, sodium ricinoleoamphoacetate, sodium stearoamphoacetate, sodium tallowamphoacetate, sodium undecylenamphoacetate, sodium wheat germamphoacetate, sodium cocoyl glycinate (Amilite GCS-11, Ajinomoto), or any mixtures thereof.

These compounds are generally available from a variety of sources or can be prepared by methods known in the art.

Particularly preferred amphoglycinates that are commercially available include:

Sodium Oliveamphoacetate (CAS No: 252750-70-1). Trade names:
Kamapure Olive (Kama International Corp), Vamasoft olive (VaMa Farma Cosmetica, Italy);
Sodium Sunflowerseed Amphoacetate (CAS No: 252768-55-3). Trade name: Kamapure Sunflowers (Kama International Corp);
Sodium Cocoabutter Amphoacetate (CAS No: 252768-69-9). Trade name: Kamapure Cocoa (Kama International Corp);
Sodium Sesame Amphoacetate. Trade Name: Kamapure Sesame (Kama International Corp);
Sodium Sweetalmond Amphoacetate (CAS No 252768-53-1). Trade Name: Kamapure Sweet Almond (Kama International Corp); and
Sodium Cocoyl Glycinate (Amilite GCS-11, Ajinomoto).

The technical or trade name vs. INCI names of some of the above are listed below:

| Technical/Trade Name | INCI Name |
| --- | --- |
| Caproamphoglycinate | Sodium caproamphoacetate |
| Caprylamphoglycinate | Sodium caprylamphoacetate |
| Cocoamphoglycinate | Sodium cocoamphoglycinate |
| Isostearoamphoglycinate | Sodium isostearoamphoacetate |
| Lauroamphoglycinate | Sodium lauroamphoacetate |
| Miristoamphoglycinate | Sodium myristoamphoacetate |
| Oleoamphoglycinate | Sodium oleoamphoacetate |
| Sodium palmamphoacetate | Sodium palmamphoacetate |
| Sodium peanutamphoacetate | Sodium peanutamphoacetate |
| Sodium ricinoleoamphoacetate | Sodium ricinoleoamphoacetate |
| Stearoamphoglycinate | Sodium stearoamphoacetate |
| Tallowamphoglycinate | Sodium tallowamphoacetate |
| Undecylenoamphoglycinate | Sodium undecylenamphoacetate |
| Disodium wheatgermamphoacetate | Disodium wheatgermamphoacetate |

Preferably, the effective amount of the dihydroacetone is about 1 wt. % to about 10 wt. % of the sunless tanning composition and the effective amount of the amphoglycinate is about 1 wt. % to about 30 wt. % of the sunless tanning composition.

In another preferred embodiment, the sunless tanning composition can further have a cosmetically acceptable vehicle, which can be up to 98 wt. % of the sunless tanning composition.

The enhancing composition may further include one or more additional components, including, but not limited to, sugars, keto-sugars, surface-active agents, polymers, softening agents, moisturizers, water-proofing agents, vitamins, sweet orange citroflavonoids, hesperitine, ozone stressed yeast lysate, *Saccharomyces cerevisiae* ferment filtrate lysate, methylsulfonyl methane (MSM), also known as dimethyl sulfone and methyl sulfone, UV filters, skin penetration agents, or any combinations thereof. Preferably, these one or more additional components are present in an amount up to about 30 wt. % of the total weight of the enhancing composition.

Preferably, the additional sunscreen can be, but is not limited to, one or more of the following:

dibenzoylmethane, oxybenzone, sulisobenzone, dioxybenzone, menthyl anthranilate, para aminobenzoic acid (PABA) ester, benzophenone-3, butyldibenzoylmethane (Parsol 1789), dimethyl cinnamate, octyl methoxycinnamate, DEA methoxycinnamate, octocrylene, drometrizole trisiloxane, octyl salicylate, homomethyl salicylate, octyl dimethyl PABA, TEA salicylate, 4-methyl benzilidene camphor, 3-benzylidene camphor, benzylidene camphor sulfonic acid ester, octyl triazone, phenyl benzimidazole sulfonic acid ester, terephthalydiene dicamphor sulfonic acid ester, di-t-butyl hydroxybenzylidene camphor, ethyl PABA, butylmethoxy dibenzoylmethane (avobenzone), terephthalydiene methylene bis-benzotriazoyltetramethylbutyl-phenol, diethylhexyl-2,6-naphthalate, bis-ethylhexyloxyphenol methoxyphenol triazine, hydroxy methylphenyl benzotriazole, methylene bis-benzotriazoyltetramethylbutylphenol, bis-ethylhexyloxyphenol methoxyphenol triazine, hydroxybenzophenone, a benzotriazole, a dibenzoyl methane, an oxanilide, a hydroxy cinnamate, oil dispersible titanium dioxide, oil dispersible zinc oxide, a silicone-anchored sunscreen, para aminobenzoic acid (PABA), salicylic acid, TEA salicylate, benzylidene camphor sulfonic acid, phenyl benzimidazole sulfonic acid, terephthalydiene dicamphor sulfonic acid, hydroxy cinnamic acid, any derivatives thereof, or any combinations thereof.

Other suitable additives include antioxidants, such as, erythrobic acid, sodium metabisulfite, sodium sulfite, rosemary extract, tocopherol, a derivative of tocopherol including a tocotriene, carotene, a carotenoid, lutein or lutein ester, a carotenoid, a phenolic antioxidant, a bioflavonoid, a plant extract, or any combinations thereof;

keratolytic agents, such as, salicylic acid, resorcinol, peroxide of an organic acid, or any combinations thereof;

anti-inflammatory agents, such as, steroidal and non-steroidal anti-inflammatory agents, plant extracts that have demonstrated anti-inflammatory activity, or any combinations thereof;

vitamins, such as, Vitamin K, Vitamin C, retinol (vitamin A), tocopherol, or any combinations thereof;

emollients, such as, cetearyl octanoate, octyl palmitate, butylene glycol, propylene glycol, glycerine, glyceryl monostearate, petrolatum, caprylic triglyceride, capric triglyceride, shae butter, silicone oil, or any combinations thereof;

humectants, such as, glycerin, propylene glycol, pentylene glycol, caprylyl glycol, hexylene glycol, butylene glycol, hyaluronic acid, one or more derivatives of hyaluronic acid, or any combinations thereof;

skin penetration enhancers, such as, ozone, SEPA, butylene glycol, cis-isomer of an unsaturated fatty acid, or any combinations thereof;

emulsifiers, such as, glyceryl stearate, cetearyl alcohol, cetyl alcohol, PEG-40 stearate, or any combinations thereof;

thickening agents, such as, xanthan gum, carbomer, clay, hydroxyethyl cellulose, or any combinations thereof;

preservatives, such as, an alkyl paraben, an alcohol, salts of benzoic acid, salts of sorbic acid, or any combinations thereof;

colorants, such as, synthetic and natural colorants including surface-treated or hydrophobically modified colorants, or any combinations thereof;

organic acids and their derivatives, such as citric acid, glycolic acid, glutamic acid, gluco Delta lactone, or any combinations thereof;

chelating agents, such as, disodium EDTA; pH adjusters, such as, an acid, a base, a buffer, or any combinations thereof, to adjust and maintain the pH to about 3.0 to about 7.5; and fragrances.

Additional additives include one or more of proteins, peptides, amino acids, colorants, pigments, including photochromic and thermo-chromic colorants and pigments, and other appropriate materials.

The present compositions typically have a vehicle. The vehicle should be a cosmetically acceptable or suitable vehicle. In the context of the present invention, the term "cosmetically acceptable vehicle" or "suitable vehicle" refer to any vehicle for a drug, a cosmetic or a medicament that is suitable for use in direct, safe contact with human tissues.

The vehicle of the sunless tanning composition is preferably suitable for use in applications that require direct contact with human tissue. The tissue is preferably skin. The vehicle can be a solid, a fluid, emulsion, balm, an aerosol or a pump spray.

The solid vehicle is preferably a patch, a tape, or a powder. The fluid vehicle is preferably a liquid, a lotion, and a gel. The sunless tanning composition is preferably in a form, such as, body wash, bar soap, liquid soap, skin care preparation, cream, foam, gel, lotion, solution, emulsion, pomade, mousse, balm, stick, pump spray, aerosol spray, or any combinations thereof.

The sunless tanning composition can be organic solvent based, water based or it can be an emulsion. The preparation of such organic solvent, water, or emulsion-based compositions would be within the skill of a person having an ordinary skill in the art and therefore, are not discussed further herein. However, neither oil-in-water emulsions nor water-in-oil emulsions are described in the prior art.

The present invention is applicable to a variety of personal care products including, but not limited to sunless tanning, skin care, personal care, and cosmetics. The preferred product forms include solution, emulsion, serum, lotion, skin cleanser, body wash, body scrub, bar soap, liquid soap, skin care preparation, foam, mousse, cream, lotion, pomade, balm, stick, gel, pump spray, and aerosol spray, or any combinations thereof.

The sunless tanning compositions have a cosmetically acceptable vehicle and contain an effective amount of the sunless tanning compositions according to the present invention.

The present invention provides a method of sunless tanning having the step of topically applying to the skin an effective amount of a sunless tanning composition having dihydroacetone and an amphoglycinate (amphoacetate).

It is known that DHA reacts with amino acids, amines, polyamines, amides, peptides and proteins to produce a brownish color. However, it is the unexpected discovery of the present invention that the coloration of skin by DHA can be intensified and expedited by utilizing Amphoglycinates, such as, Vamasoft olive (VaMa Farma Cosmetica, Italy), and related compounds just before the treatment with the DHA, slightly after the treatment or simultaneously with it.

Different Amphoglycinates, which are also known as "Amphoacetates" or simply as "amphoteric surfactants," can generate products of reaction with different color characteristics, when they are allowed to react with DHA suggesting that the nature of fatty acid plays an important role in color generation, which is an unexpected discovery The sunless tanning composition of the present invention can be a single component composition where the dihydroacetone and the amphoglycinate are combined along with the other ingredients into a one-component composition, which is used as such for tanning.

Alternatively, the sunless tanning composition of the present invention can be a two-component composition having a first component and a second component. Thus, the first component in the two-component composition has the dihydroacetone and optionally the cosmetically acceptable vehicle, if present, and the second component has the amphoglycinate and further optionally the cosmetically acceptable vehicle, if present.

At least one of the first and the second components can further have one or more sugars, surface-active agents, sweet orange citroflavonoids, hesperitine, ozone stressed yeast lysate, *Saccharomyces cerevisiae* ferment filtrate lysate, polymers, softening agents, moisturizers, water-proofing agents, vitamins, UV filters, skin penetration agents, or any combinations thereof.

As described herein above, the sunless tanning composition according to the present invention can be formulated as a one-component system. It can also be formulated as a two-component system, one containing DHA and the other containing amphoglycinates formulated separately and kept separated until application time. At that time, the components are mixed and thereafter applied to the skin.

Alternatively, each component is applied successively to the skin, one after the other, in an alternating sequence. The successive applications are repeated, as desired, until a satisfactory tanning color is obtained.

Depending on the concentration of the active ingredients in the sunless tanning composition, color development starts within 4-6 min after the sunless tanning composition is applied. This is much faster that color development provided by combination of DHA and polyamines that typically starts within 30 min, a bench mark, of the application of the sunless tanning composition.

The present method provides a uniform and natural looking sunless tan over all treated skin surfaces at a rate faster than known formulations.

In addition, amphoglycinates, especially sodium oliveamphoacetate or Vamasoft olive (natural surfactant derived from olive oil), have good foaming capabilities, they respect the integrity of skin's hydrolipid barrier, and are extremely mild and non irritating to the skin in human patch tests.

The Examples that follow are illustrative of the present invention. The Examples should not be construed as being limiting in any manner whatsoever.

Example 1

In Vitro Tests

Color development in the model systems containing DHA and different amphoglycinates was evaluated after combining commercially available sunless tanner containing 5% of DHA (5 g) and different amphoglycinates (0.2 g) presented in Table 1.

Model systems were mixed until uniform and kept at 23 C. Times until the start of color development and color changes in the resulting systems were monitored.

Color readings were taken using the Minolta spectrophotometer with the following settings:

Reflectance Setting, SCI+SCE Specular Component, MAV (8 mm) Measurement Area, and 100% Full UV Setting.

The following CIELAB parameters were measured in order to evaluate the colors and their changes in the model systems:

Delta L* (lightness/darkness difference); Delta C* (total chroma difference); Delta a* that shows the red/green difference; Delta b* being the yellow/blue difference; Delta E* (total color difference) that integrates the differences between the L*, a*, and b* of the initial and developed color.

Data presented in Table 1 show that different amphoglycinates (amphoacetates) in conjunction with DHA can generate rapid color development (color development started in less than 5 min) and also different colors in model systems.

TABLE 1

Colors developed in the model systems containing DHA and different amphoglycinates (amphoacetates)

| # | Model System | dL* (D65) | dC* (D65) | da* (D65) | db* (D65) | dE*ab (D65) | Start of Color Development |
|---|---|---|---|---|---|---|---|
| 1 | 5% DHA Cream + Sodium Sweetalmond Amphoacetate | 2.8 | 9.36 | −2.05 | 8.73 | 9.39 | 4'55" |
| 2 | 5% DHA Cream + Sodium Oliveampho-acetate | 5.44 | 11.8 | −1.77 | 10.94 | 12.34 | 4'59" |
| 3 | 5% DHA Cream + Sodium Sunflowerseed Amphoacetate | 10.21 | 18.29 | −3.24 | 17.63 | 5.02 | 4'50" |
| 4 | 5% DHA Cream + Sodium Sesame Amphoacetate | 13.44 | 13.01 | −2.02 | 12.92 | 3.24 | 4'30" |

The differences in Delta L* values (lightness/darkness), Delta C* (total chroma) as well as Delta a* (red/green color coordinate) and Delta b* (yellow/blue) were very pronounced. The total color differences (Delta E*) attributed to different amphoacetates varied in the range of 3 to 12.

Sodium oliveamphoacetate generated the most dramatic total color difference (Delta E* of 12.34), followed by Sodium sweetalmond amphoacetate (with Delta E* of 9.39). These findings indicate that the nature of fatty acid in the amphoacetate structure can influence color development and color characteristics in the model systems containing DHA and specific amphoacetate.

Example 2

In Vivo Tests

Skin color developed after application of the commercially available sunless tanning product, a mousse containing 5% DHA (control), was compared with skin color developed after application of control followed by the application of 25% aqueous solutions of selected amphoglycinates (amphoacetates) presented in Table 2.

Panelists with Type 1-2 skin were employed. Their forearms were gently exfoliated, rinsed and dried. Initial (base readings) of the designated areas on each forearm were taken by Minolta spectrophotometer with the following settings: Reflectance Setting, SCI+SCE Specular Component, MAV (8 mm) Measurement Area, and 100% Full UV.

The following CIELAB parameters were measured in order to evaluate the skin colors and their changes: Delta L* (lightness/darkness difference); Delta C* (chroma difference); Delta a* that shows the red/green difference; Delta b* being the yellow/blue difference; Delta E* (total color difference) that integrates the differences between the L*, a*, and b* of the initial and developed color.

A 4 mg/cm$^2$ dose of the sunless tanner was applied to the forearms and gently rubbed into the skin using a finger-cot.

After 10 min of the application, a 2 mg/cm$^2$ of the solution of the tested amphoglycinates were applied on the designated areas (12 sq.cm) and gently rubbed into the skin. Color measurements were taken again using Minolta spectrophotometer after 14 hrs after application.

The "natural universe" of tan and tonality data presented on the graphs as solid black lines was obtained from a study conducted by Estee Lauder (Muizzuddin N, Marenus K, Maes D. Tonality of suntan vs. sunless tanning with dihydroxyacetone. Skin Research and Technology 2000; 6: 199-204). "Natural universe" of color was determined by the color achieved from a natural suntan.

Figure 2:
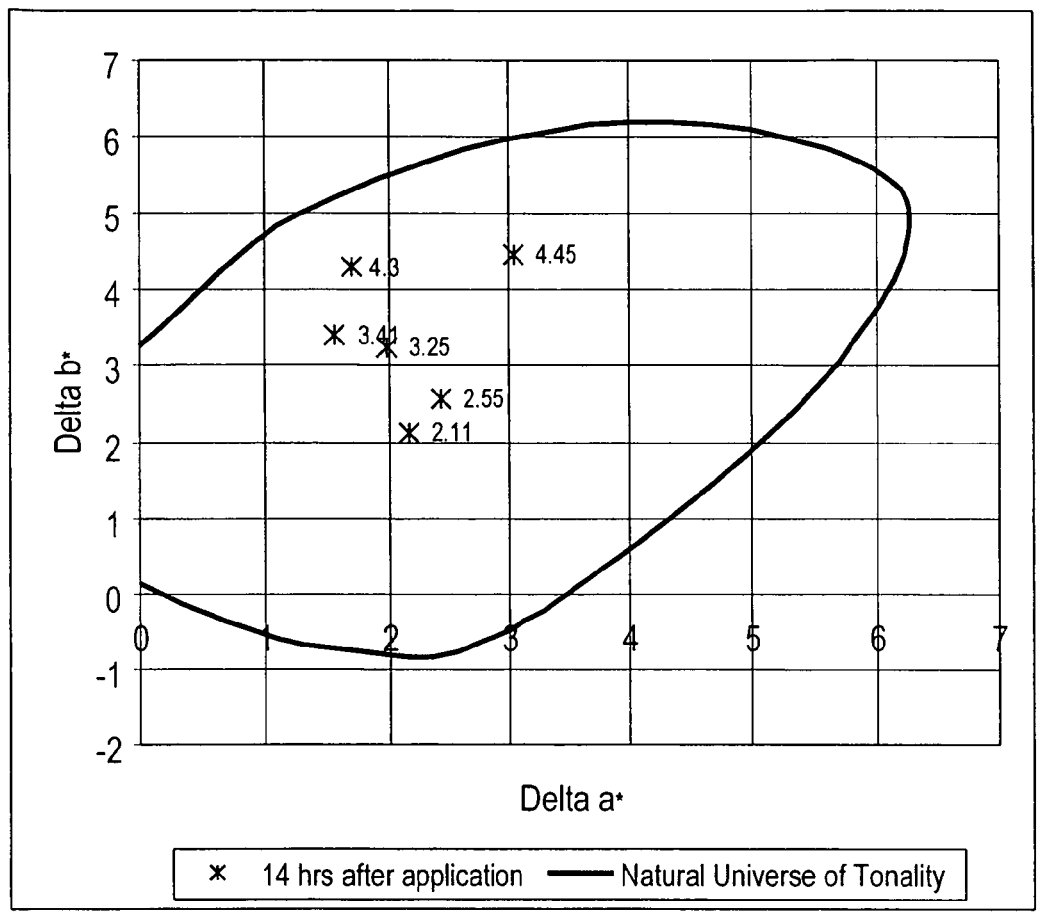
FIG. 2 is CIELAB plot of Delta b* versus Delta a*. It shows the color characteristics of the skin treated with DHA-product alone or in conjunction with amphoacetates

Referring to Table 2, FIG. 1 and FIG. 2, it can be seen that different amphoglycinates in conjunction with DHA can generate various skin tones that differ from the color generated by DHA containing formulation alone (control).

In the Figures the CIELAB color space model has been utilized. Widely accepted CIELAB color space is used within the cosmetic industry to evaluate skin colors. The CIELAB color space is a three dimensional space, where every color can be located. The location of any color in the space is determined by its color coordinates: L*, a*, and b*, where:

L*—the lightness/darkness coordinate;

a*—the red/green coordinate, with +a* indicating red and −a* indicating green;

b*—the yellow/blue coordinate, with +b* indicating yellow, and −b* indicating blue.

CIELAB total color difference is the distance between the color locations, which can be expressed as Delta E, where:

$$\text{Delta } E^* = (\text{Delta } L^{*2} + \text{Delta } a^{*2} + \text{Delta } b^{*2})^{1/2}.$$

Delta E* is a total color difference, which integrates the differences between the L*, a*, and b* of the initial skin (sample) color and skin (sample) color that was developed. C* is the chroma coordinate: $C^* = [(a^*)^2 + (b^*)^2]^{1/2}$, and Delta C* is the total chroma difference between the initial and developed color. Delta L* indicates the lightness/darkness difference.

Positive value (+) of Delta L* means that developed color is lighter than initial and negative (−) Delta L* means that developed color is darker than initial. Delta a* shows the red/green difference. Positive value (+) of Delta a* indicates that developed color is redder (or less green) than initial and negative (−) Delta a* value means that developed color is less red (or greener) than initial. Delta b* describes the yellow/blue difference. Positive value (+) of Delta b* indicates that developed color is yellower (or less blue) than initial and negative (−) Delta b* means that developed color is less yellow (or bluer) than initial.

FIG. 1 is CIELAB plot of Delta C* versus Delta L*. It shows total chroma and lightness changes of the skin treated with DHA-product alone or in conjunction with amphoacetates.

"Natural universe" of color determined by the skin color achieved from a natural suntan (or actual sun exposure) is used in the present invention as the reference.

Referring to FIG. 1, it can be seen that the tan achieved with the use of sunless tanner in conjunction with sodium sweetalmond amphoacetate (dL* 2.95; dC* 3.27), sodium cocoyl glycinate (dL* 1.86; dC* 3.74), sodium sunflowerseed amphoacetate (dL* 3.28; dC* 3.73), and sodium sesame amphoacetate (dL* 1.14; dC* 2.73), are different but did fall within this "natural universe" of color characteristics (dL* and dC*) developed after actual sun exposure and presented on the FIG. 1 as solid black line.

Interestingly, skin tone generated by the control (dL* 0.44; dC* 4.63) was outside of "natural universe" of color.

Referring to FIG. 2, it can be seen that it is CIELAB plot of Delta b* versus Delta a*. It shows the color characteristics of the skin treated with DHA-product alone or in conjunction with amphoacetates. Delta b* and Delta a* values indicate that the tan achieved with the use of sunless tanner in conjunction with sodium sweetalmond amphoacetate (db* 2.55; da* 2.44), sodium cocoyl glycinate (db* 3.41; da* 1.56), sodium sunflowerseed amphoacetate (db* 3.25; da* 1.98), sodium sesame amphoacetate (db* 2.11; da* 2.17) and sodium oliveamphoacetate (db* 4.45; da* 3.05) are different from the color changes induced by control (db* 4.3; da* 1.71) and did fall within this "natural universe" of color characteristics (db* and da*) developed on skin after actual sun exposure and presented on the FIG. 2 as solid black line.

Table 2 shows the differences in skin tones developed after application of the sunless tanner alone and in conjunction with amphoacetates.

TABLE 2

Differences in skin tones

| # | Data Name | dL* (D65) | dC* (D65) | da* (D65) | db* (D65) | dE*ab (D65) |
|---|---|---|---|---|---|---|
| 1 | 5% DHA Mousse (Control) | 0.44 | 4.63 | 1.71 | 4.3 | 4.65 |
| 2 | 5% DHA Mousse + Sodium Sweetalmond Amphoacetate | 2.95 | 3.27 | 2.44 | 2.55 | 4.6 |
| 3 | 5% DHA Mousse + Sodium Cocoyl Glycinate | 1.86 | 3.74 | 1.56 | 3.41 | 4.18 |
| 4 | 5% DHA Mousse + Sodium Oliveamphoacetate | 1.04 | 5.26 | 3.05 | 4.45 | 5.49 |
| 5 | 5% DHA Mousse + Sodium Sunflowerseed Amphoacetate | 3.28 | 3.73 | 1.98 | 3.25 | 5.02 |
| 6 | 5% DHA Mousse + Sodium Sesame Amphoacetate | 1.14 | 2.73 | 2.17 | 2.11 | 3.24 |

These findings described above indicate that the nature of fatty acid in the amphoacetate structure can influence skin color development and skin color characteristics when products containing DHA are used in conjunction with specific amphoacetate, which is an unexpected and useful discovery.

Example 3

Various DHA-containing and amphoglycinate-containing types of formulas can be utilized in sunless tanning systems in different delivery system and packages, such as, creams, lotions, solutions, sprays/wipes, dual-chamber tubes and aerosols. Composition with Amphoglycinate that can be used as the part of sunless tanning system comprises two cosmetic formulations, one containing DHA and one containing one or more amphoglycinates that can be mixed at the time of use or also to be applied successively to the skin, as a leave on or a wash-off formulation, one after the other.

Composition with Amphoacetate (Amphoglycinate):

| Ingredient | Wt % |
|---|---|
| Amphoacetate (Amphoglycinate) | 0.1-30 |
| Glycerin | 1-20 |
| Cocamidopropyl Betaine (30%) | 0-5 |
| Lauric Acid | 0-1 |
| Myristic Acid | 0-1 |
| Glycol Distearate | 0-5 |
| Behenyl Alcohol | 0-5 |
| Polyquaternium-39 (10%) | 0-1 |
| Citric Acid | 0-1 |
| Pentylene Glycol | 0-5 |
| Water | to 100 |

The amphoglycinate can be one or more of the following: sodium oliveamphoacetate, sodium sunflowerseed amphoacetate, sodium cocoabutter amphoacetate, sodium sesame amphoacetate, sodium sweetalmond amphoacetate, sodium caproamphoacetate, sodium capryloamphoacetate, sodium isostearoamphoacetate, sodium lauroamphoacetate, sodium myristoamphoacetate, sodium oleoamphoacetate, sodium palmamphoacetate, sodium peanutamphoacetate, sodium ricinoleoamphoacetate, sodium stearoamphoacetate, sodium tallowamphoacetate, sodium undecylenamphoacetate, sodium wheat germamphoacetate, sodium cocoyl glycinate, or any mixtures thereof.

Example 4

A one-component formulation was prepared as follows:

At room temperature DHA was added to the water, mixed until dissolved. Hydroxyethylacrylate/sodium (and) Acryloyldimethyltaurate Copolymer (and) Squalane (and)

Polysorbate-60 were added under vigorous agitation and continued mixing for 10-15 min. PPG-11 stearyl ether was then added slowly followed by amphoglycinate, preservative and fragrance.

One-Component Formulation

This composition is formed immediately after mixing all of the ingredients at once for immediate use.

| Ingredient: | Wt. %: |
|---|---|
| Water | Q.s. to 100.00 |
| Dihydroacetone | 1.00-10.00 |
| Hydroxyethylacrylate/sodium (and) Acryloyldimethyltaurate copolymer (and) Squalane (and) Polysorbate-60 | 2.00-3.00 |
| PPG-11 Stearyl Ether | 4.00-6.00 |
| Amphoglycinate | 1.00-2.00 |
| Preservative$^a$ | 0.50-1.00 |
| Fragrance | 0-0.20 |

Preservative$^a$: Phenoxyethanol (and) Methylparaben (and) Ethylparaben (and) Propylparaben (and), Butylparaben (and) isobutylparaben Example 5

A two-component formulation was prepared as follows:

Components of Phase A and B were combined in two separate vessels, heated to 70-75° C. with mixing until uniform and combined at 70-75° C. with homogenization. The combined phases were cooled to 40° C. with mixing. Phase C was added at 40° C. with mixing until uniform.

This composition is formed as two component formulations:

COMPONENT A, which is the first component of the two-component formulation and COMPONENT B, which is the second component of the two-component formulation.

COMPONENT A and COMPONENT B are mixed just prior to use to produce a final composition having all of the necessary ingredients for immediate use.

Thereafter, the final composition is applied immediately after mixing.

| COMPONENT A | |
|---|---|
| | Wt %: |
| Phase A: | |
| Glyceryl Stearate (and) PEG-100 Stearate | 3.00-4.00 |
| Caprylic Capric Triglycerides | 3.50-4.50 |
| C12-15 Alkyl Benzoate | 2.00-3.00 |
| Cetyl Alcohol | 2.00-3.00 |
| PEG-7 Glyceryl Cocoate | 0.30-0.50 |
| Dimethicone | 0.30-1.00 |
| Stearic Acid | 0.60-1.00 |
| Petrolatum | 0-1.20 |
| Stearyl Alcohol | 1.90-2.10 |
| Steareth-2 | 0.20-0.30 |
| Steareth-20 | 0.30-0.40 |
| Tocopherol | 0.10-0.50 |
| Preservative$^a$ | 0.50-1.00 |
| Phase B | |
| Water | Qs to 100.00 |
| Aloe Vera Juice | 0.10-1.00 |
| Disodium EDTA | 0.05-0.10 |
| Phase C: | |
| Water | 10.00-12.00 |
| Propylene Glycol | 3.00-5.00 |
| Dihydroacetone | 1.00-10.00 |
| Fragrance | 0-0.30 |
| Citric Acid | Qs to a pH of 3.5-4.5 |

Preservative$^a$: Phenoxyethanol (and) Methylparaben (and) Ethylparaben (and) Propylparaben (and), Butylparaben (and) Isobutylparaben

| COMPONENT B | |
|---|---|
| | Wt %: |
| Phase A: | |
| Glyceryl Stearate (and) PEG-100 Stearate | 3.00-4.00 |
| Caprylic Capric Triglycerides | 3.50-4.50 |
| C12-15 Alkyl Benzoate | 2.00-3.00 |
| Cetyl Alcohol | 2.00-3.00 |
| PEG-7 Glyceryl Cocoate | 0.30-0.50 |
| Dimethicone | 0.30-1.00 |
| Stearic Acid | 0.60-1.00 |
| Petrolatum | 0-1.20 |
| Stearyl Alcohol | 1.90-2.10 |
| Steareth-2 | 0.20-0.30 |
| Steareth-20 | 0.30-0.40 |
| Tocopherol | 0.10-0.50 |
| Preservative$^a$ | 0.50-1.00 |
| Phase B | |
| Water | Qs to 100.00 |
| Aloe Vera Juice | 0.10-1.00 |
| Disodium EDTA | 0.05-0.10 |
| Phase C: | |
| Water | 10.00-12.00 |
| Propylene Glycol | 3.00-5.00 |
| Amphoglycinate | 1.00-10.00 |
| Fragrance | 0-0.30 |
| Citric Acid | Qs to a pH of 3.5-4.5 |

Preservative$^a$: Phenoxyethanol(and) Methylparaben(and) Ethylparaben(and) Propylparaben(and) Butylparaben (and) Isobutylparaben.

It should be understood that the foregoing description is only illustrative of the present invention. Various alternatives and modifications can be devised by those skilled in the art without departing from the present invention. Accordingly, the present invention is intended to embrace all such alternatives, modifications and variations that fall within the scope of the appended claims.

What is claimed is:

1. A sunless tanning composition consisting of:
   dihydroacetone;
   an amphoglycinate selected from the group consisting of sodium oliveamphoacetate, sodium sunflowerseed amphoacetate, sodium cocoabutter amphoacetate, sodium sesame amphoacetate, sodium sweetalmond amphoacetate, sodium caproamphoacetate, sodium capryloamphoacetate, sodium isostearoamphoacetate, sodium lauroamphoacetate, sodium myristoamphoacetate, sodium oleoamphoacetate, sodium palmamphoacetate, sodium peanutamphoacetate, sodium ricinoleoamphoacetate, sodium stearoamphoacetate, sodium tallowamphoacetate, sodium undecylenamphoacetate, sodium wheat germamphoacetate, sodium cocyl glycinate, and any mixtures thereof;
   a cosmetically acceptable vehicle selected from the group consisting of water, organic solvent, and a combination thereof; and optionally, at least one additional ingredient selected from the group consisting of:
  an emulsifier selected from the group consisting of glyceryl stearate, cetearyl alcohol, cetyl alcohol, PEG-40 stearate, and any combinations thereof,
  a humectant selected from the group consisting of glycerin, propylene glycol, pentylene glycol, caprylyl glycol, hexylene glycol, butylene glycol, hyaluronic acid, one or more derivatives of hyaluronic acid, and any combinations thereof, and
  a preservative selected from the group consisting of alkyl paraben, alcohol, benzoic acid salt, sorbic acid salt, and any combinations thereof.

2. The sunless tanning composition of claim 1, wherein said dihydroacetone is about 1 wt % to about 10 wt % of the sunless tanning composition.

3. The sunless tanning composition of claim 1, wherein said amphoglycinate is about 1 wt % to about 30 wt % of the sunless tanning composition.

4. The sunless tanning composition of claim 1, wherein said cosmetically acceptable vehicle is present in an amount of up to 98 wt % of the sunless tanning composition.

5. The sunless tanning composition of claim 1, wherein said at least one additional ingredient is present in an amount of up to 30 wt % of the sunless tanning composition.

6. The sunless tanning composition of claim 1, wherein the composition has a first component and a second component separate from said first component, wherein said dihydroacetone and said cosmetically acceptable vehicle are in said first component, and wherein said amphoglycinate and said cosmetically acceptable vehicle are in said second component.

7. The sunless tanning composition of claim 6, wherein at least one of said emulsifier and said humectant are in at least one of said first and said second components.

8. The sunless tanning composition of claim 1, wherein said sunless tanning composition is a product selected from the group consisting of solution, emulsion, serum, lotion, skin cleanser, body wash, body scrub, bar soap, liquid soap, skin care preparation, foam, mousse, cream, lotion, pomade, balm, stick, gel, pump spray, and aerosol spray, and any combinations thereof.

9. A method of sunless tanning comprising the step of:
topically applying to the skin an effective amount of a sunless tanning composition, wherein said sunless tanning composition consists of:
  dihydroacetone;
  an amphoglycinate selected from the group consisting of sodium oliveamphoacetate, sodium sunflowerseed amphoacetate, sodium cocoabutter amphoacetate, sodium sesame amphoacetate, sodium sweetalmond amphoacetate, sodium caproamphoacetate, sodium capryloamphoacetate, sodium isostearoamphoacetate, sodium lauroamphoacetate, sodium myristoamphoacetate, sodium oleoamphoacetate, sodium palmamphoacetate, sodium peanutamphoacetate, sodium ricinoleoamphoacetate, sodium stearoamphoacetate, sodium tallowamphoacetate, sodium undecylenamphoacetate, sodium wheat germamphoacetate, sodium cocyl glycinate, and any mixtures thereof;
  a cosmetically acceptable vehicle selected from the group consisting of water, organic solvent, and a combination thereof; and
  optionally, at least one additional ingredient selected from the group consisting of:
    an emulsifier selected from the group consisting of glyceryl stearate, cetearyl alcohol, cetyl alcohol, PEG-40 stearate, and any combinations thereof,
    a humectant selected from the group consisting of glycerin, propylene glycol, pentylene glycol, caprylyl glycol, hexylene glycol, butylene glycol, hyaluronic acid, one or more derivatives of hyaluronic acid, and any combinations thereof, and
    a preservative selected from the group consisting of alkyl paraben, alcohol, benzoic acid salt, sorbic acid salt, and any combinations thereof.

10. The method of claim 9, wherein said dihydroacetone is present in an amount of about 1 wt % to about 10 wt % of the sunless tanning composition.

11. The method of claim 9, wherein said amphoglycinate is present in an amount of about 1 wt % to about 30 wt % of the sunless tanning composition.

12. The method of claim 9, wherein said cosmetically acceptable vehicle is up to 98 wt % of the sunless tanning composition.

13. The method of claim 9, wherein said at least one additional ingredient is present in an amount of up to 30 wt % of the sunless tanning composition.

14. The method of claim 9, wherein said sunless tanning composition has a first component and a second component separate from said first component, wherein said dihydroacetone and said cosmetically acceptable vehicle are in said first component, and wherein said amphoglycinate and said cosmetically acceptable vehicle are in said second component.

15. The method of claim 14, wherein at least one of said emulsifier and said humectant are in at least one of said first and said second components.

16. The method of claim 9, wherein said sunless tanning composition is a product selected from the group consisting of solution, emulsion, serum, lotion, skin cleanser, body wash, body scrub, bar soap, liquid soap, skin care preparation, foam, mousse, cream, lotion, pomade, balm, stick, gel, pump spray, and aerosol spray, and any combinations thereof.

17. A sunless tanning composition consisting of:
  about 1 wt % to about 10 wt % of dihydroacetone;
  about 1 wt % to about 30 wt % of an amphoglycinate selected from the group consisting of sodium oliveamphoacetate, sodium sunflowerseed amphoacetate, sodium cocoabutter amphoacetate, sodium sesame amphoacetate, sodium sweetalmond amphoacetate, sodium caproamphoacetate, sodium capryloamphoacetate, sodium isostearoamphoacetate, sodium lauroamphoacetate, sodium myristoamphoacetate, sodium oleoamphoacetate, sodium palmamphoacetate, sodium peanutamphoacetate, sodium ricinoleoamphoacetate, sodium stearoamphoacetate, sodium tallowamphoacetate, sodium undecylenamphoacetate, sodium wheat germamphoacetate, sodium cocyl glycinate, and any mixtures thereof;
  a cosmetically acceptable vehicle selected from the group consisting of water, organic solvent, and a combination thereof; and
  up to 30 wt % of at least one additional ingredient selected from the group consisting of glyceryl stearate, cetearyl alcohol, cetyl alcohol, PEG-40 stearate, glycerin, propylene glycol, pentylene glycol, caprylyl glycol, hexylene glycol, butylene glycol, hyaluronic acid, derivatives of hyaluronic acid, alkyl paraben, alcohol, benzoic acid salt, sorbic acid salt, and any combinations thereof.

* * * * *